United States Patent
Schliefer

(10) Patent No.: US 7,815,798 B2
(45) Date of Patent: Oct. 19, 2010

(54) DISCRETE DROP DISPENSING DEVICE AND METHOD OF USE

(75) Inventor: Arthur Schliefer, Portola Valley, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 235 days.

(21) Appl. No.: 12/170,775

(22) Filed: Jul. 10, 2008

(65) Prior Publication Data
US 2010/0006502 A1   Jan. 14, 2010

(51) Int. Cl.
*B01D 15/08* (2006.01)
(52) U.S. Cl. .............. 210/198.2; 210/656; 222/199; 222/420; 239/4; 239/102.1; 422/70; 422/100
(58) Field of Classification Search ............ 210/635, 210/656, 137, 198.2; 222/199, 420; 239/4, 239/102.1; 356/316; 422/70, 100
See application file for complete search history.

(56) References Cited

U.S. PATENT DOCUMENTS

| | | | | |
|---|---|---|---|---|
| 4,934,564 A | * | 6/1990 | Piatt | 222/14 |
| 6,509,562 B1 | * | 1/2003 | Yang et al. | 250/287 |
| 6,540,153 B1 | * | 4/2003 | Ivri | 239/4 |
| 6,569,385 B1 | * | 5/2003 | Little et al. | 422/100 |
| 6,917,165 B2 | * | 7/2005 | Hopwood et al. | 315/111.21 |
| 2005/0195393 A1 | * | 9/2005 | Karanassios | 356/316 |
| 2006/0176341 A1 | * | 8/2006 | Juch et al. | 347/68 |

* cited by examiner

*Primary Examiner*—Ernest G Therkorn

(57) ABSTRACT

A discrete drop dispensing device comprises a substrate comprising an upper surface and a lower surface and orifices extending from the upper surface to the lower surface, adapted to receive a fluid at a flow rate. The discrete drop dispensing device also comprises an oscillator disposed adjacent to the substrate and configured to vibrate the substrate to expel drops having a substantially equal volume of the fluid. The flow rate is substantially identical to a drop dispensing rate. A method and a device for performing liquid chromatography are also described. The method comprises automatically adjusting the drop dispensing rate to a change in the flow rate or a change in a composition of a mobile phase of the fluid.

6 Claims, 7 Drawing Sheets

DISCRETE DROP DISPENSING DEVICE AND METHOD OF USE

BACKGROUND

Chemical and biological separations are routinely performed in various industrial and academic settings to determine the presence and/or quantity of individual species in complex sample mixtures. There exist various techniques for performing such separations.

One particularly useful analytical process is chromatography, which encompasses a number of methods that are used for separating ions or molecules for analysis. Liquid chromatography ('LC') is a physical method of separation wherein a liquid 'mobile phase' carries a sample containing a mixture of compounds or ions for analysis (analytes) through a separation medium or 'stationary phase.' Stationary phase material typically includes a liquid-permeable medium such as packed granules (particulate material) or a micro-porous matrix (e.g., porous monolith) disposed within a tube or similar boundary. The resulting structure including the packed material or matrix contained within the tube is commonly referred to as a 'separation column.' In the interest of obtaining greater separation efficiency, so-called 'high performance liquid chromatography' ('HPLC') methods often utilizing high operating pressures are commonly used.

Often an electro-spray system is used as in the interface between the LC device and a mass spectrometer. In electro-spray systems, a voltage is applied to the mobile phase to charge the mobile phase. As the fluid comprising the mobile phase and analytes exits a tube or channel, a Taylor cone is formed and the fluid forms a stream, which, in a short distance, will start to breakup into small droplets. The mobile phase droplets have a charge and, as the mobile phase begins to evaporate, the charge can be transferred to the analytes.

In electro-spray systems there is no need to account for the accuracy of the flow rate, or changes in flow rate due to the composition of the mobile phases, or changes in mobile phase composition during a mobile phase gradient program.

The majority of ions formed by the electrospray process are mobile phase or solvent ions. Because a limited number of charged molecules can be accepted by the mass spectroscopy (MS) inlet a charge competition between the ions of interest and the mobile phase ions can result.

Because of the shortcomings of known electro-spray systems, LC/MS interfaces in which the mobile phase is not charged have been investigated. In particular, the fluid effluent is transformed into the gas-phase, and only the analytes are ionized. Unfortunately, prior attempts to form a gas or vapor phase of the mobile phase and analytes have certain drawbacks.

One such drawback results from the inconsistency of the volume of the drops of fluid provided. Various factors can impact the volume of the drops, including but not limited to, flow rate of the fluid from the LC column and the composition of the fluid, which can vary depending on the selection of the mobile phase. As should be appreciated, the flow rate can be consistent, but inaccurate, due to design and manufacturing variations in the pumping systems. In addition, during a run, the composition of the mobile phase can change in a programmed gradient where the percentage of one type of mobile phase changes with respect to another type of mobile phase, such as starting from a mobile phase of 100% methanol and 0% water, and over time, changing the mobile phase to 0% methanol and 100% water.

What is needed, therefore, is a drop formation device for dispensing fluid from an LC column that overcomes at least the drawbacks of known devices described above.

BRIEF DESCRIPTION OF THE DRAWINGS

The present teachings are best understood from the following detailed description when read with the accompanying drawing figures. The features are not necessarily drawn to scale. Wherever practical, like reference numerals refer to like features.

DEFINED TERMINOLOGY

It is to be understood that the terminology used herein is for purposes of describing particular embodiments only, and is not intended to be limiting.

As used in the specification and appended claims, the terms 'a', 'an' and 'the' include both singular and plural referents, unless the context clearly dictates otherwise. Thus, for example, 'a device' includes one device and plural devices.

In this specification and in the claims that follow, reference will be made to a number of terms that shall be defined to have the following meanings:

The term 'LC' as used herein refers to a variety of liquid chromatography devices including, but not limited to, HPLC devices;

The term 'flow-rate' as used herein refers to a volume of a fluid per unit time;

The term 'drop rate' as used herein refers to the number of drops that are formed by the discrete drop dispensing device per unit time; and The term 'drop dispensing rate' as used herein refers to the number of drops of a fluid dispensed per unit time multiplied by the volume per drop.

DETAILED DESCRIPTION

In the following detailed description, for purposes of explanation and not limitation, representative embodiments disclosing specific details are set forth in order to provide a thorough understanding of the present teachings. Descriptions of known systems, devices, materials, methods of operation and methods of manufacture may be omitted so as to avoid obscuring the description of the example embodiments. Nonetheless, systems, devices, materials and methods that are within the purview of one of ordinary skill in the art may be used in accordance with the representative embodiments.

Figure 1:
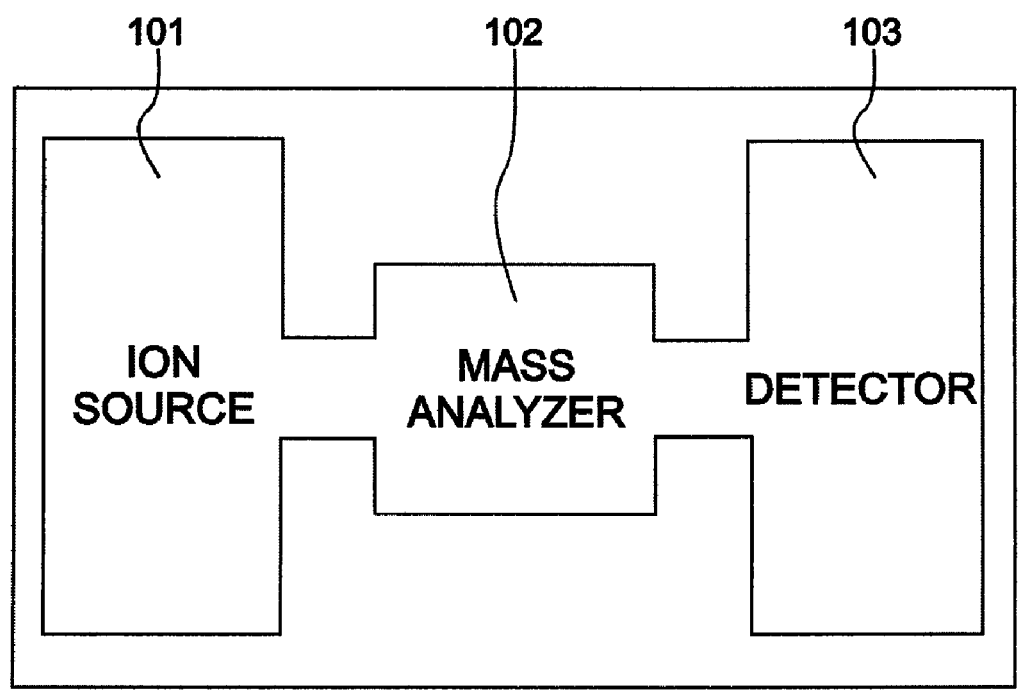
FIG. 1 is a simplified schematic diagram of a mass spectrometer in accordance with a representative embodiment.

FIG. 1 shows a simplified schematic diagram of a mass spectrometer 100 in accordance with a representative embodiment. The block diagram is drawn in a more general format because the present teachings may be applied to a variety of different types of mass spectrometers. As should be appreciated as the present description continues, devices and methods of representative embodiments may be used in connection with the mass spectrometer 100. As such, the mass spectrometer 100 is useful in garnering a more comprehensive understanding of the functions and applications of the devices and method of the representative embodiments, but is not intended to be limiting of these functions and applications.

The mass spectrometer 100 includes an ion source 101, a mass analyzer 102 and a detector 103. The ion source 101 will be described in more detail below. The mass analyzer 102 may include a conduit such as a sleeve, transport device, dispenser, capillary, nozzle, hose, pipe, pipette, port, connector, tube, orifice, orifice in a wall, coupling, container, housing, structure or other apparatus used to transport ions from the ion source 101 to the detector 103. Such apparatuses are known to one of ordinary skill in the art and are not described in detail to avoid obscuring the description of representative embodiments. The detector 103 may be a known ion detector used to detect the analyte ions that are collected and transported by the mass analyzer 102. The detector 103 may also include known hardware, software or firmware, or a combination thereof useful in detecting analytes.

Figure 2:
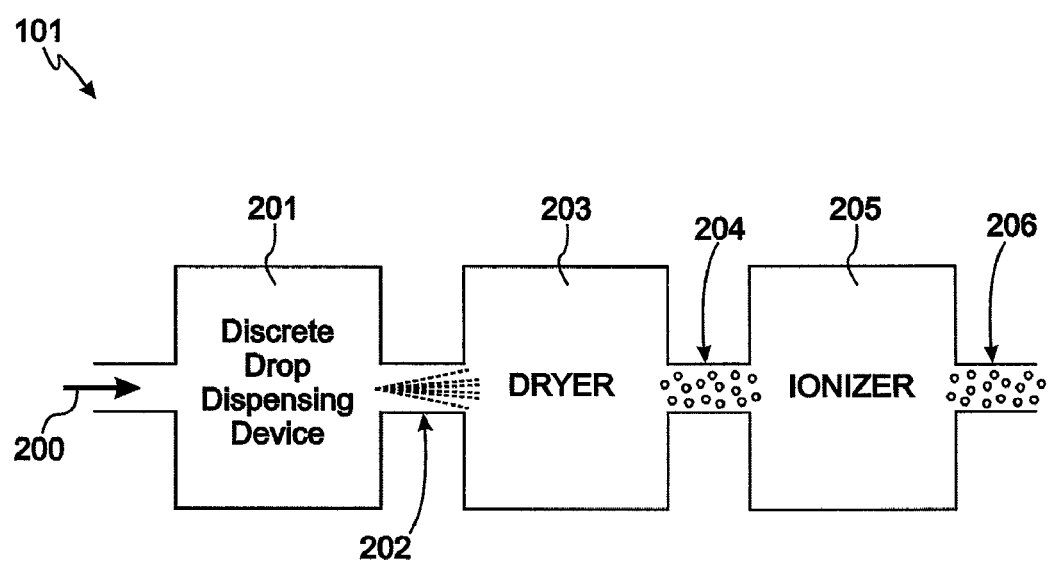
FIG. 2 is a simplified schematic diagram of an ionizer in accordance with a representative embodiment.
Figure 3A:
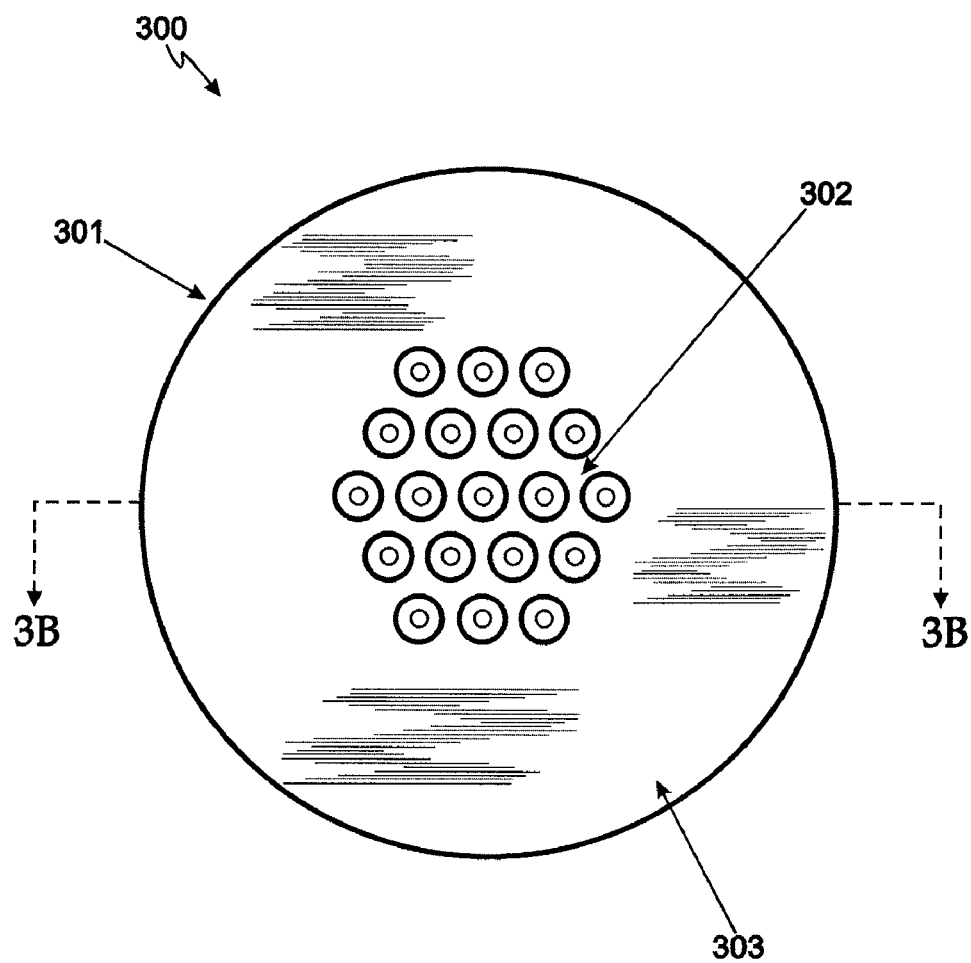
FIG. 3A is a top view of a disk of a discrete drop dispensing device in accordance with a representative embodiment.
Figure 3B:
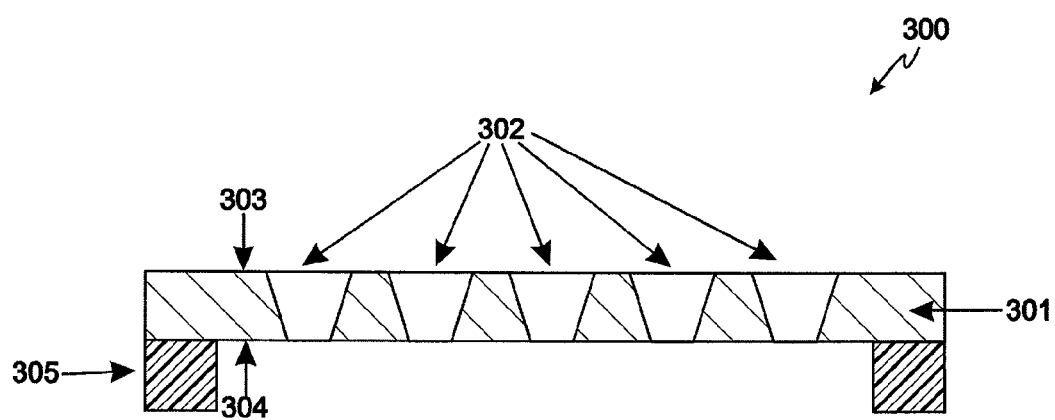
FIG. 3B is a cross-sectional view of the disk shown in FIG. 3A along the line 3B-3B.
Figure 4A:
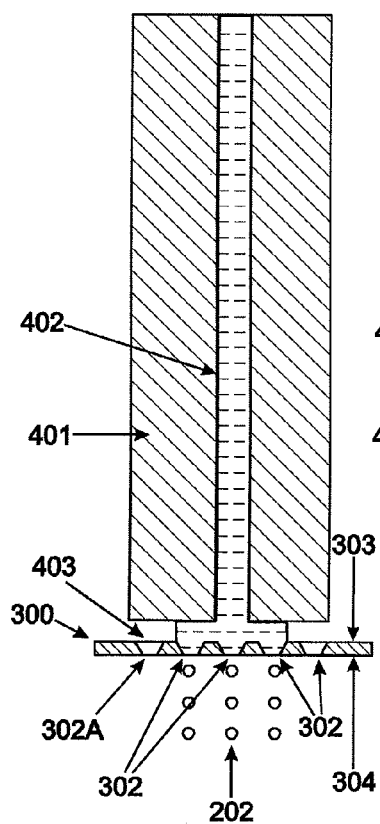
FIGS. 4A-4C show cross-sectional views of a discrete drop dispensing device receiving fluid from an LC column in accordance with a representative embodiment.
Figure 4B:
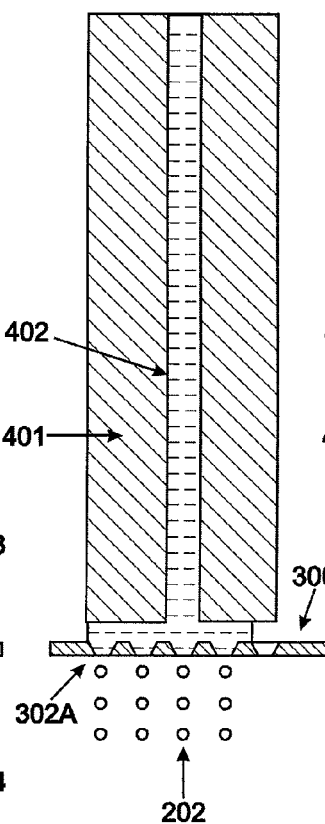

FIG. 2 shows a simplified schematic diagram of the ion source 101 in accordance with a representative embodiment. The ion source 101 includes a discrete drop dispensing device 201 that forms and dispenses drops 202 of the fluid, which are transformed into an aerosol (aerosolized) without substantially ionizing the fluid 201. The ion source 101 further comprises a dryer 203 that dries the aerosol drops to obtain a gas-phase mobile phase and gas-phase analytes 204 and an ionizer 205 that ionizes the gas-phase analytes to obtain analyte ions 206 that are drawn into the mass analyzer 102 for transfer to the detector 103.

FIG. 3A shows a top view of a disk 300 used in the discrete drop dispensing device 201 in accordance with a representative embodiment. The disk 300 comprises a substrate 301 defining orifices 302 extending from a surface 303 through a thickness of the disk 300 to a surface (not shown in FIG. 3A) opposite the surface 303. The disk 300 is illustratively circular, although other shapes are contemplated. The orifices 302 are shown to be located substantially symmetrically about the center of the circular disk with a certain center-to-center spacing or pitch. In other embodiments, the orifices are arranged differently to accommodate specific considerations. The number of orifices can vary as well. Notably, the shape of the disk 300, the location of the orifices 302, and the pattern of the orifices 302 may be tailored to the configuration of the discrete drop dispensing device 201, or to other design considerations. Furthermore, the disc may be made of one or more of a variety of materials, including but not limited to stainless steel, glass, plastic, or ceramic materials.

FIG. 3B shows the disk 300 in cross-section along the line 3B-3B in FIG. 3A. Orifices 302 are illustratively conical in cross-section with the greater diameter opening located at the surface 303 and the lesser diameter opening located at the opposing surface 304. As will become clearer as the present description continues, fluid from an LC column or similar conduit is provided at the surface 303 of the disk 300. The disk 300 is mechanically vibrated by an oscillator 305 thereby dispensing drops of the fluid 201 from the openings at the opposing surface 304. Beneficially, the drops dispensed from the orifices 302 are of substantially consistent volume when the parameters of the solvent, such as surface tension, viscosity, and temperature, are held substantially constant. The dispensed drops are then dried and the analytes ionized for analysis by the detector 103.

Illustratively, the oscillator 305 comprises an actuator or an electro-mechanical transducer and a source of an alternating drive waveform. In a specific embodiment, the electromechanical transducer comprises a piezoelectric element. The oscillator 305 is disposed either annularly about the disk or at diametrically opposed locations along a side of substrate 301, beneath surface 304 (as shown) or over surface 303 and may comprise a piezoelectric oscillator connected to appropriate driver circuitry to cause oscillation. One illustrative example of such an oscillator and its arrangement is described in U.S. Pat. No. 6,540,153 to Irvi, the disclosure of which is specifically incorporated herein by reference.

The number and size of the orifices 302 are determined considering the flow rate of the fluid from the LC and the composition of the fluid. As described in greater detail below, a greater flow rate requires a greater drop dispensing rate by the discrete drop dispensing device 201. Two ways to control the drop dispensing rate is by controlling the number of drops dispensed per unit time and the volume of the drops dispensed. Therefore, larger orifices will provide larger drop volumes and more orifices will provide more drops. It follows that fewer orifices, or smaller orifices, or both, will reduce the drop dispensing rate. It is noted that other factors can influence the volume of the drops and the rate of their dispensing.

The volume of the drops dispensed by the discrete drop dispensing device 201 is influenced by the composition of the fluid and such parameters as surface tension, viscosity, and temperature. The drop volume can also be varied by the amplitude of the drive waveform applied to the oscillator used to vibrate the disk 300. The drop rate can also be controlled by changing the duty cycle of the drive waveform applied to the oscillator. Normally, the discrete drop dispensing device 201 is operated at or near a resonant frequency of the disk. In an example, the oscillator frequency was 128 kHz. The drop rate can be reduced by discontinuing the drive waveform applied to the actuator/transducer of the oscillator for a percentage of the time.

FIGS. 4A-4C show cross-sectional views of the discrete drop dispensing device 201 receiving fluid from an LC column 401 having fluid 402 therein according to a representative embodiment. The cross-sectional views illustrate the function of the discrete drop dispensing device 201. As will become clearer as the present description continues, the discrete drop dispensing device 201 self-corrects the drop dispensing rate from the disk 300 to compensate for comparatively small mismatches in the flow rate of the LC and the nominal drop dispense volume of the drop formation device. These mismatches may be due to consistent, but inaccurate flow rates from the LC. In addition, discrete drop dispensing device 201 will compensate for a change in the flow rate of the LC column, or change in composition of fluid 402 from the LC column 401, or both. Variations in the drop dispensing rate are described in conjunction with FIGS. 4A-4C.

In FIG. 4A, the fluid 402 is provided at an initial flow rate and exits the LC column 401 to a region 403 between the lower surface of the LC column 401 and surface 303 of the disk 300. Exiting the LC column 401, fluid 402 will accumulate in the region 403 between the lower surface of the LC column 401 and surface 303 of the disk 300. As the disk 300 is vibrated by the oscillator 305, the fluid 402 in the region 403 or portion thereof that is in contact with the surface 303 of the disk 300 will be ejected as drops 202. The fluid volume that is dispensed is drops from the device 300 will be replaced with more of the fluid 402 exiting the LC column 401.

FIG. 4B illustrates the condition where the flow rate of the fluid 402 from the LC column 401 is slightly greater than the drop dispensing rate. The increased volume of fluid causes the volume of the fluid accumulated in the region 403 to increase so that, at some point, the accumulated fluid comes in contact with an orifice 302A of the disk 300. For a short period, the drop dispensing rate may increase due to the additional drops' being dispensed from orifice 302A, thereby reducing the volume in region 403 until the orifice 302A is no longer in contact with the fluid accumulated in region 403. Ultimately, the self-correcting nature of the discrete drop dispensing device 201 results in a return to the condition described in conjunction with FIG. 4A.

Figure 4C:
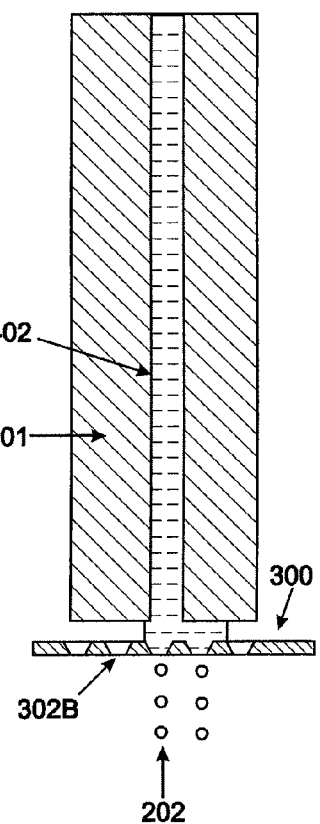

FIG. 4C illustrates the condition where the flow rate of the fluid 402 from the LC column 401 is slightly less than the drop dispensing rate. A decrease in the flow rate of the fluid 402 from the LC column 401 causes the volume of the fluid accumulated in the region 403 to decrease so that eventually the accumulated fluid is no longer contacts orifice 302B. The drop dispensing rate will temporally decrease and the volume of fluid accumulated in region 403 will increase until orifice 302B is again in contact with the accumulated fluid. Again, the self-correcting nature of the discrete drop dispensing device 201 causes the condition of FIG. 4A to recur.

As described above, a mismatch of the flow rate of fluid 402 from LC column 401 and the drop dispense rate of drops 202 can be caused simply by difficulty matching the consistent, but often inaccurate, continuous flow rate from the LC column to the discrete drop dispensing rate of the discrete drop dispensing device 201. Additionally or alternatively, it is possible for the drop dispensing rate to change during an LC analysis due to a gradient program where the mobile phase composition changes over time. The change in mobile phase composition is likely to cause a change in the volume of the drops formed by the discrete drop dispensing device 201. This can result in the occurrence of the conditions shown in and described in connection with FIGS. 4B-4C. However, the change of drop volume is accommodated in a self-correcting manner as described and the analysis can continue during these changes.

If the volume per unit drop decreases due to a change in the mobile phase composition, but the drop rate remains the same, the drop dispensing rate decreases. This can cause an increase in the volume of fluid 402 accumulated in region 403 and the occurrence of FIG. 4B. However, because of the self correcting nature of the drop dispensing device 201, the increased volume of fluid 402 causes the volume of the fluid accumulated in region 403 to increase so that, at some point, the accumulated fluid comes in contact with an orifice 302A of the disk 300. For a short period, the drop dispensing rate may increase, reducing the volume in region 403 until the orifice 302A is no longer in contact with the fluid in region 403, and the condition returns to that of FIG. 4A.

If the volume per unit drop increases due to a change in the mobile phase composition, and drops per unit time remains the same, the drop dispensing rate increases. This can cause a decrease in the volume of fluid 404 accumulated in region 403 and the condition shown in FIG. 4C. However, because of the self-correcting nature of the discrete drop dispensing device 201, the decreased volume of the fluid causes the volume of the fluid 404 accumulated in the region 403 to decrease and so that eventually the accumulated fluid no longer contacts orifice 302B. The drop dispensing rate may temporally decrease and the volume of fluid in region 403 will increase until orifice 302B is again in contact with the fluid. This causes the condition of FIG. 4A to recur.

Figure 5:
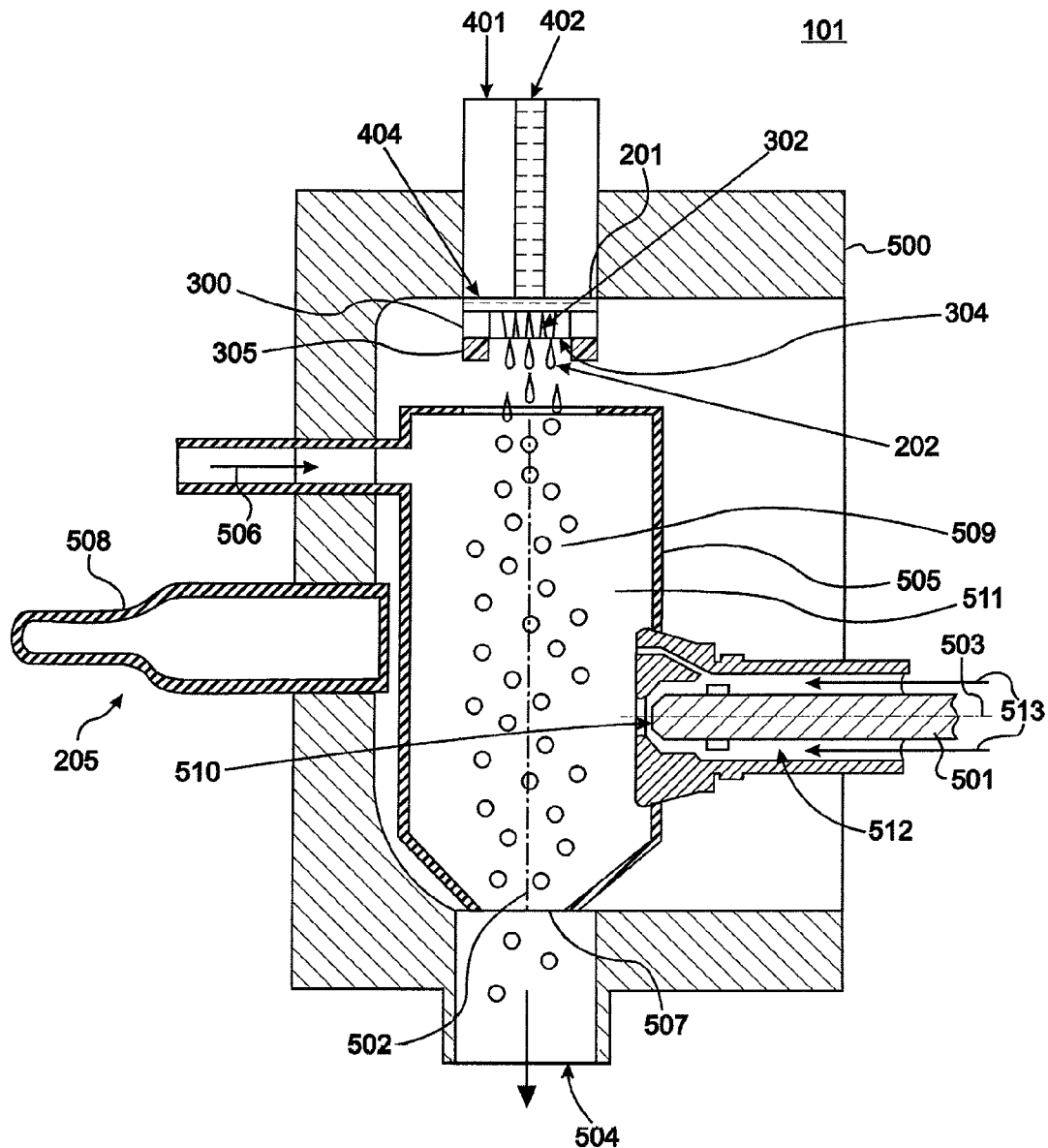
FIG. 5 is a cross-sectional view of an ionizer in accordance with a representative embodiment.

FIG. 5 is a cross-sectional view of an ion source 101 in accordance with a representative embodiment. The ion source 101 comprises a housing 500 and the discrete drop dispensing device 201 such as described in connection with FIGS. 3A-4C. 4C. The discrete drop dispensing device 201 dispenses drops 202 in response to vibrations provided by oscillator 305 and is arranged substantially orthogonally to a conduit 501 (shown as a capillary) of the mass analyzer 102. In a representative embodiment, the discrete drop dispensing device 201 is oriented along a "drop longitudinal axis" 502 that is substantially orthogonal to a conduit longitudinal axis 503 of the conduit 501. The term "drop longitudinal axis" refers to the theoretical axis or line that can be drawn through the region having the greatest concentration of molecules in the direction of drops 202. While the orthogonal arrangement may be used, it is not essential. A variety of angles (obtuse and acute) may be defined between the drop longitudinal axis 502 and the longitudinal axis 503 of the conduit 501. Alternatively, the drop longitudinal axis 502 may be aligned with the longitudinal axis 503 of the conduit 501. The pressure in the housing 500 is maintained at about 20 Torr to about 2000 Torr. Operation at atmospheric pressure (around 760 Torr) and non-atmospheric pressure is thus possible. The housing 500 has an exhaust port 504 for removal of gases.

The ion source 101 of the presently described embodiment comprises a drying tube 505. The drying tube 505 may be a separate component or may be integrated with the housing 500. The drying tube 505 is positioned adjacent to the lower surface 304 of the discrete drop dispensing device 201 for receiving the drops 202, which are aerosolized and dried as described above. The drying tube 505 may be heated by a heater (not shown). The heater may include, but is not limited to, an infrared (IR) lamp, a heated surface, a turbo spray device, and a microwave lamp.

Alternatively or additionally, the drying tube 505 may be heated by flowing a hot inert carrier gas 506 through the drying tube 505. When flowed through the drying tube 505, the carrier gas also serves to guide or direct the aerosolized fluid drops towards an outlet 507 of the drying tube 505. The drying tube 505 turns the aerosolized fluid drops into a gas-phase mobile phase and a gas-phase analytes 509. The heat input required to dry the mobile phase of the fluid may be calculated based on the drop volume of the discrete drop dispensing device 201 and the mobile phase composition. Beneficially, the gas-phase mobile phase is substantially without any charge since the aerosolized fluid is not affirmatively subjected to any electric potential. In the present embodiment, the ionizer 205 comprises a light source 508, such as at least one ultraviolet (UV) lamp. The light source 508 may also include, but is not limited to, a krypton light source, an argon light source, and a helium light source. In a specific embodiment, the light source 508 may be a microplasma UV source such as described in commonly-owned U.S. patent application Ser. No. 11/932,835, entitled "Microplasma Illumination Device and Method" to Viorica Lopez-Avila, et al. and filed Oct. 31, 2007. The disclosure of this application is specifically incorporated herein by reference.

In such an embodiment, the light source 508 may be inside drying tube 505 with a gas line provided through the wall of the drying tube 505 and the wall of the housing. Providing the light source 508 inside the drying tube allows its windowless properties, which enable the emission of comparatively very short wavelength UV radiation, to be exploited. The light source 508 may be positioned in a number of locations downstream from the discrete drop dispensing device 201 adjacent to a portion of the drying tube 505 where the aerosolized fluid has dried sufficiently to transform into the gas-phase mobile and gas-phase analytes 509. This portion of the drying tube 505 defines an ionization region 511. The wavelength of the LV light generated by light source 508 is selected such that the UV light at least substantially ionizes the gas-phase analytes 509 to produce analyte ions without substantially ionizing the gas-phase mobile phase. In other words, usefully, the gas-phase analyte 509 is strongly ionized while the gas-phase mobile phase is minimally ionized, if at all.

The mass analyzer 102 may include the conduit 501 or any number of capillaries, conduits or devices for receiving and moving the analyte ions from the ionization region to the detector 103. The conduit 501 is disposed in the housing 500 downstream from the discrete drop dispensing device and illustratively opposite to the light source 508. The conduit 503 comprises an orifice 510 that receives the analyte ions and transports them to the detector 103. Optionally, a gas conduit 512 may direct a drying gas 513 toward the ions in the ionization region. This drying gas 513 interacts with the analyte ions in the ionization region to remove any mobile phase remaining from the aerosolized fluid provided from the discrete drop dispensing device 201.

Figure 6:
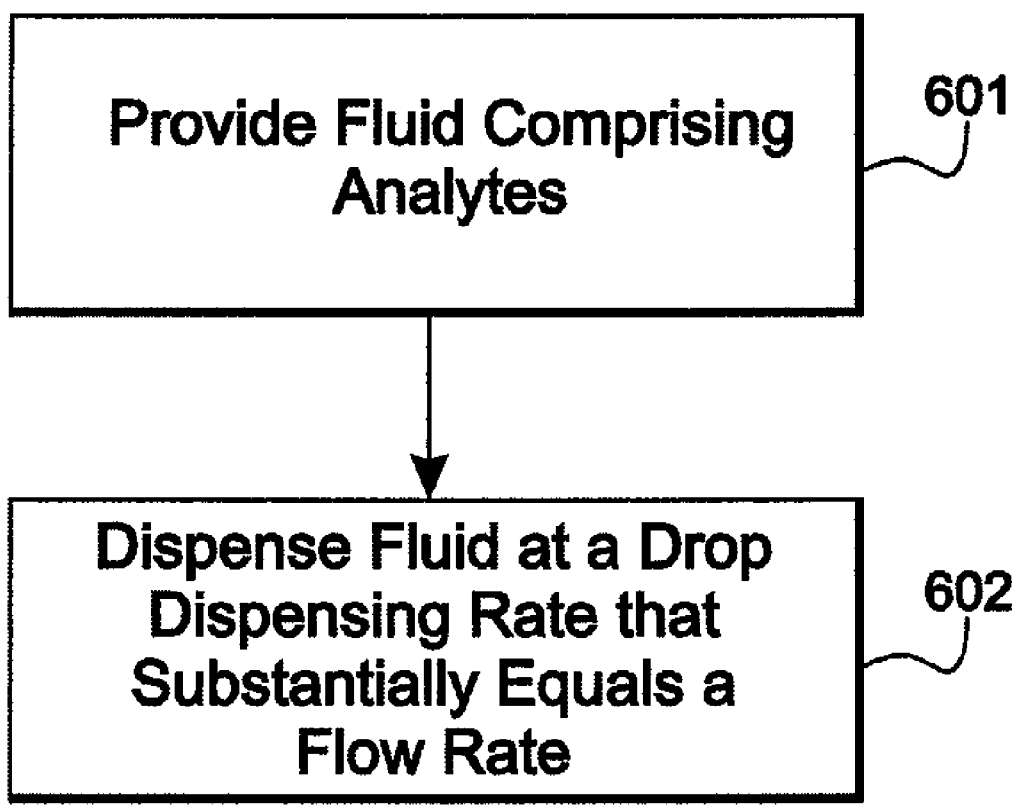
FIG. 6 is a flow-chart of a method in accordance with a representative embodiment.

FIG. 6 is a flow-chart of a method in accordance with a representative embodiment. The method is implemented using the various components, structures and arrangements thereof described in representative embodiments in conjunction with in FIGS. 1-5. The details of the function of the embodiments of these embodiments are not repeated in order to avoid obscuring the presently described embodiments.

At 601, the method comprises providing a fluid comprising analytes at a flow rate to a discrete drop dispensing device 201, such as from an LC column 401. At 602 the method comprises dispensing drops (e.g., drops 202) of the fluid comprising a substantially similar volume from the discrete drop dispensing device at a drop dispensing rate. Beneficially, the flow rate is substantially identical to the drop dispensing rate.

A discrete drop dispensing device, an ion source comprising the discrete drop dispensing device, a device for performing liquid chromatography and a method are described in conjunction with various representative embodiments. The discrete drop dispensing device provides drops at a drop dispensing rate that is substantially equal to the flow rate of the fluid from the LC. If the LC flow rate is slightly less than the drop dispensing rate, the drop dispensing rate will decrease; and if the LC flow rate increases, the drop dispensing rate will also increase in a self-correcting manner. This way, the drop dispensing rate will self regulate, dispensing a little more or a little less fluid for a short period. This self-regulation occurs rapidly and the average drop dispense rate will be substantially constant over the time periods of the measurement. Having multiple orifices on the disk also allows a wider dynamic range of LC flow rates to be dispensed. Additionally, and as described, changes in mobile phase composition result in changes in the drop dispensing rate so that the flow rate and drop dispensing rate will remain substantially the same; and the average drop dispense rate remains substantially constant over time periods of measurement.

In view of this disclosure it is noted that the methods and devices can be implemented in keeping with the present teachings. Further, the various components, materials, structures and parameters are included by way of illustration and example only and not in any limiting sense. In view of this disclosure, those skilled in the art can implement the present teachings in determining their own applications and needed components, materials, structures and equipment to implement these applications, while remaining within the scope of the appended claims.

The invention claimed is:

1. A device, comprising:
an ion source for obtaining ions of an analyte comprising:
a discrete drop dispensing device, comprising:
a substrate comprising an upper surface and a lower surface; and orifices extending from the upper surface to the lower surface, adapted to receive a fluid at a flow rate; an oscillator disposed adjacent to the substrate and configured to vibrate the substrate to expel drops each having a substantially equal volume of the fluid, wherein the flow rate is substantially identical to a drop dispensing rate;
a dryer that dries the fluid to obtain a gas-phase mobile phase and a gas-phase analyte; and
an ionizer that ionizes the gas-phase analyte to obtain ions thereof.

2. A device as claimed in claim 1, wherein the discrete drop dispensing device further comprises an oscillator disposed adjacent to the substrate.

3. A device as claimed in claim 1, wherein the oscillator comprises a piezoelectric oscillator configured to vibrate the substrate.

4. A device as claimed in claim 1, wherein the drop dispensing rate of the fluid changes with a change in the flow rate.

5. A device as claimed in claim 1, wherein a change in a composition of the fluid changes the volume of the drops.

6. A device as claimed in claim 1, wherein a change in the flow rate to a second flow rate results in a change in the drop dispensing rate to a second drop dispensing rate that is substantially identical to the second flow rate.

* * * * *